United States Patent [19]

Fung

[11] Patent Number: 5,314,335
[45] Date of Patent: May 24, 1994

[54] DENTAL CROWN

[76] Inventor: John Fung, 627 George Street, Sydney, NSW 2000, Australia

[21] Appl. No.: 969,186
[22] PCT Filed: Jul. 5, 1991
[86] PCT No.: PCT/AU91/00300
§ 371 Date: Feb. 11, 1993
§ 102(e) Date: Feb. 11, 1993
[87] PCT Pub. No.: WD92/03102
PCT Pub. Date: Mar. 5, 1992

[30] Foreign Application Priority Data

Aug. 16, 1990 [AU] Australia .............................. PK1780

[51] Int. Cl.$^5$ ............................ A61C 5/10; A61C 5/08
[52] U.S. Cl. .................................... 433/223; 433/218
[58] Field of Search ................... 433/218, 219, 222.1, 433/223

[56] References Cited

U.S. PATENT DOCUMENTS

| | | | |
|---|---|---|---|
| 2,105,398 | 1/1938 | Barrett et al. | 433/222.1 |
| 2,194,790 | 3/1940 | Gluck | 433/223 X |
| 4,392,829 | 7/1983 | Tanaka | 433/222 |
| 4,459,112 | 7/1984 | Shoher et al. | 433/223 X |
| 4,834,656 | 5/1989 | Loudon | 433/223 X |
| 4,846,718 | 7/1989 | Rieger | 433/223 X |

FOREIGN PATENT DOCUMENTS 3608992 10/1986 Fed. Rep. of Germany ......... A61C 5/10

OTHER PUBLICATIONS

The American Text Book of Prosthetic Dentistry, Ed C. R. Turner, published by Henry Kempton 4th Ed., 1913, pp. 703–715, See particularly FIG. 703.
Guide to Dental Materials & Devices, 8th Ed 1976–1978, published by American Dental Association, p. 116, last paragraph.

*Primary Examiner*—Gene Mancene
*Assistant Examiner*—Nicholas D. Lucchesi
*Attorney, Agent, or Firm*—Wagner & Middlebrook

[57] ABSTRACT

A construction applicable to dental crowns, facings, inlays, and the like including a stainless steel wire mesh (3) shaped to fit closely over a prepared tooth remnant (1), and being integrally bonded to a cavity (11) of a crown body (4) so as to form an integral crown (5) ready for use. The integral crown (5) can be adhered to the remnant (1) in a conventional manner, for instance by using dental filler. The body (4) and mesh (3) are very strongly joined by a mechanical interlock action by virtue of the mesh texture.

9 Claims, 2 Drawing Sheets

DENTAL CROWN

REFERENCE TO RELATED PATENT APPLICATIONS

This is a United States national filing of PCT application AU91/0300, filed Jul. 5, 1991, based upon Australian application PK 1780, filed Aug. 16, 1990.

FIELD OF THE INVENTION

This invention relates to the construction of dental prostheses. A wide variety of crowns, inlays, facings and similar structures can be produced in accordance with the invention.

PRIOR ART

When replacing a portion of a damaged tooth, for example by the use of a dental crown, either one of two practices are common. The dental crown can be produced wholly from porcelain having an outer shape moulded to approximately the desired tooth shape and an inner cavity which is inserted over and cemented to the tooth preparation which is ground from the natural tooth. Alternatively, a porcelain cap is formed by painting a porcelain mixture over a metal core, such as foil or mesh, which has been formed so as to be cemented to the tooth preparation, and firing the cap to harden the porcelain and bond the porcelain to the core. While the second mentioned alternative is superior from a functional point of view as it can bear some mastication force, it is inferior from an aesthetic point of view.

DESCRIPTION OF INVENTION

The present invention, in one broad form, can be described as a dental prosthesis (defined herein as a crown, inlay, facing or the like) comprising an outer body functionable as a tooth, or part thereof, formed separately from and being fused or bonded to an initially partially flexible, textured insert which can be cemented to a tooth remnant.

By textured, it is meant that the interface between the insert and the body has a texture to provide a positive mechanical interlock.

It is preferred that the insert is stainless steel mesh, or other corrosion resistant tensile material mesh. The mesh supports the porcelain as well as provides a strong mechanical interlocking of the porcelain to the mesh by way of the oxide bonding material.

In one preferred embodiment the body is porcelain cast to approximately a desired tooth shape and is bonded to the mesh by baked porcelain. In an alternative preferred embodiment the body is porcelain formed about the mesh by baking to approximate a desired tooth shape.

The completed prosthesis device may be bonded to a prepared tooth remnant using dental cement, filling material or adhesive.

The prosthesis may be in a number of forms including a full crown, an inlay, a cosmetic facing, or an integral tip and facing.

In another broad form the invention can be described as a method of manufacturing a dental prosthesis comprising:

shaping a textured corrosion resistant flexible insert in a general cup shape so as to fit over an outer surface of a prepared tooth remnant, forming a dental outer body and bonding the body to the insert.

Preferably, in one alternative, the forming and bonding of the body occur as one step. In another alternative the body is semi-formed before inserting the insert and then finally fired causing bonding of the body to the insert.

The body may be a heat fusible porcelain.

The insert may be stainless steel mesh.

In one procedure, the tooth remnant is prepared and a mould taken in rubber, or the like. The mesh is then custom shaped in a dental laboratory to suit the mould before inserting the mesh into the body for final firing. The custom crown, or the like, is then a substantially perfect fit to the prepared remnant.

In an alternative procedure, a dental surgery is supplied with a range of sizes of fully formed crowns, or the like, from which an appropriate size is selected to suit the remaining teeth. The mesh will be sized according to the tooth size so as to ensure adequate strength, and the tooth remnant is prepared to be just slightly smaller than the mesh. Dental filling material, or the like, is placed in the cavity defined by the mesh and the crown, or the like is pressed into place on the remnant and held still for the curing period.

DESCRIPTION OF DRAWINGS

By way of example only, various embodiments of the invention will be described with reference to the accompanying drawings in which.

DESCRIPTION OF PREFERRED EMBODIMENTS

Figure 1:
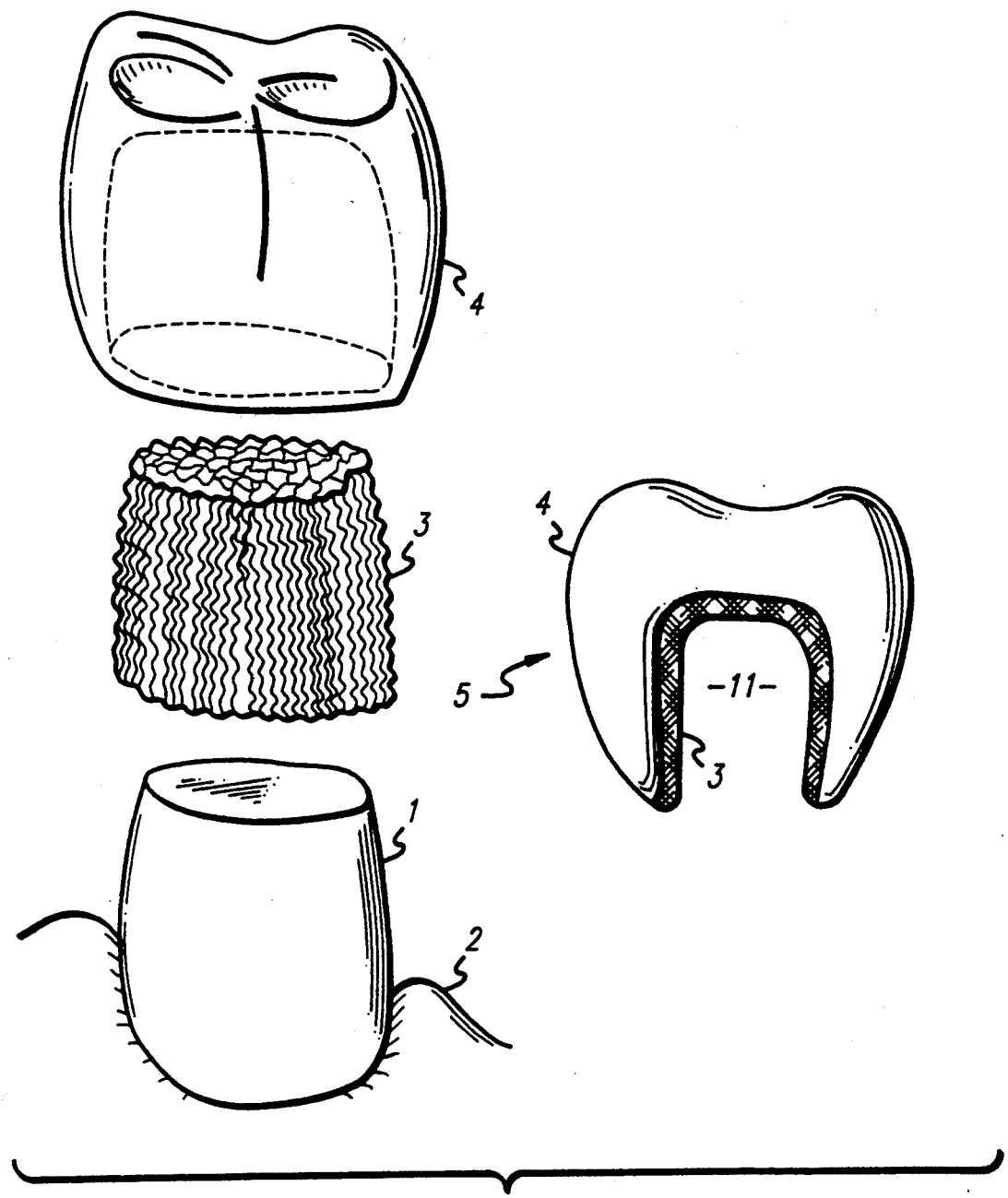
FIG. 1 is a disassembled sketch of a prosthetic crown remnant in accordance with the invention.

FIG. 1 shows a tooth preparation 1 in the patient's jaw 2, the post having already been prepared by conventional dental grinding techniques to form a strong, healthy post to which the crown may be attached.

A porcelain crown 4 is shaped so as to simulate the functioning and appearance of the natural tooth in a healthy condition. Intermediate the post 1 and the crown 4 is a stainless steel mesh skeleton 3 which is bonded in a mechanically interlocking manner, by virtue of its mesh structure, to the inside cavity of the crown 4. The complete crown 5 incorporating the stainless steel mesh 3 and the porcelain crown 4 is adhered to the post 1 by using conventional dental cement, filling material or adhesive.

The flexibility of the stainless steel (or other suitable material) mesh 3 provides a complete crown structure 5 which has much more give than does a crown produced by conventional techniques. Thus, crown 5 is much less likely to failure. Moreover, because the texture of the mesh provides an interlocking bond with the porcelain, if damage does occur to the porcelain it will tend to remain wholly fixed in place rather than fragment and become loose in the patient's mouth.

The relatively thin thickness of the stainless steel mesh 3 allows a relatively thick body of porcelain in the crown 4 and thus provides very good aesthetics qualities which are much closer to those of natural teeth than is the case of traditional crowns formed on solid metal cores.

Also to improve aesthetics, the porcelain material may be specified such as an outer enamel porcelain layer, intermediate dentine porcelain layer, and inner opaque porcelain encasing the mesh 3.

The completed crown 5 can be formed and fitted in any one of a variety procedures. Standard porcelain shells 4 can be produced in varying sizes and shapes and kept on hand in the dental surgery. The stainless steel mesh 3 is shaped to suit a prepared tooth preparation 1, and a thin layer of porcelain mixture painted on to the mesh, which is then inserted into a suitable pre-made shell 4 and baked. The pre-made shell 4 may have been partially fired in which case this baking step not only bonds the mesh 3 to the shell 4, but also completes the firing of the shell 4. This baking and finishing procedure will likely require only approximately one hour and can then be bonded to the tooth preparation using dental cement. Thus a high quality, permanent crown can be fitted in a single visit to the dental surgery.

In a particularly time efficient procedure, completed, fully fixed crowns 5 are produced in a dental laboratory in a variety of sizes for each tooth type. The mesh 3 for these crowns 5 will be sized according to the outer size of the crown 5 so as to ensure sufficient porcelain thickness for strength, but as large as possible inner cavity 11 so as to allow as large as possible tooth remnant 1. In the surgery the dentist selects the appropriately sized crown 5 and prepares the remnant 1 to the appropriate size being just slightly smaller than the cavity 11. Dental filling material is placed into the cavity 11 and the crown 5 put in place on the remnant 1.

The filler material is plastic, or paste like, and fills in any space between the mesh 3 and the remnant 1. The filler material cures, normally in about 5 minutes, and the job is complete.

Thus the patient may select to have a custom shaped crown in order to best duplicate the true shape of the natural tooth being repaired or a cheaper but equally strong alternative. In all cases the crown may be mechanically superior to previously known crowns.

Figure 2:
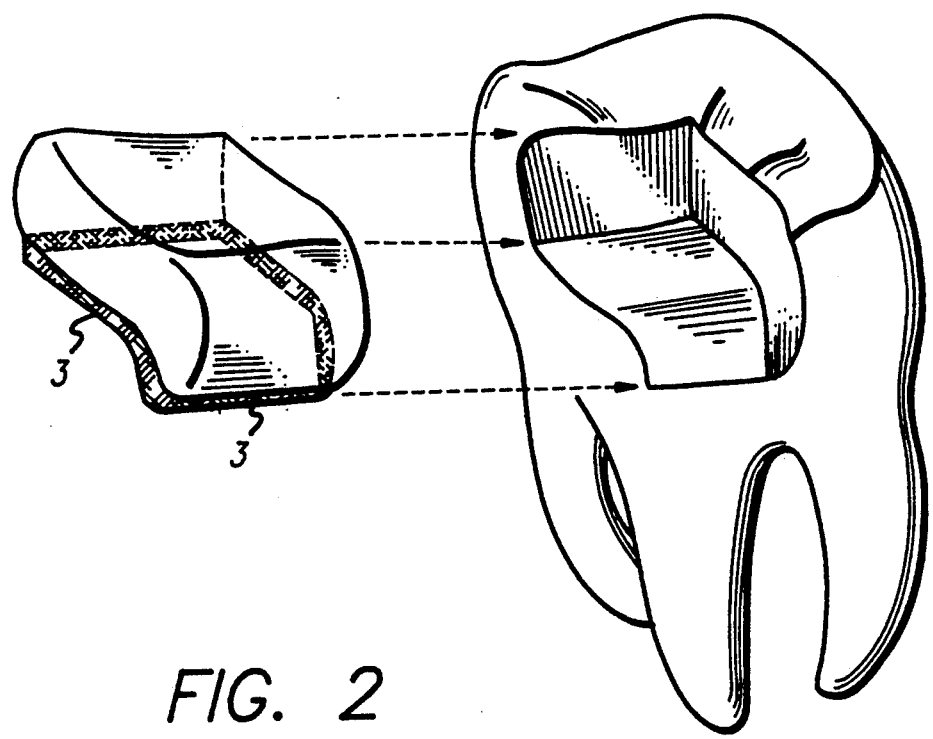
FIG. 2 is a diagrammatic sketch of an inlay according to the present invention.

FIG. 2 shows an application of the invention in which an inlay is applied to the damaged portion of a tooth where the damage is not so extensive as to require a complete crown. The damaged section of the tooth is ground out using traditional methods. After preparing the natural tooth remnant in this way, the stainless steel mesh 3 is shaped so as to fit the prepared surface area to be inlaid. Next, a premoulded porcelain inlay can be baked onto the mesh by firstly painting a thin layer of porcelain mixture to the mesh 3.

Once the inlay mesh/porcelain composite is finished, it can be adhered to the prepared tooth using dental cement.

Such an inlay produces a repair of very high aesthetic quality and very good functional strength and durability.

Figure 3:
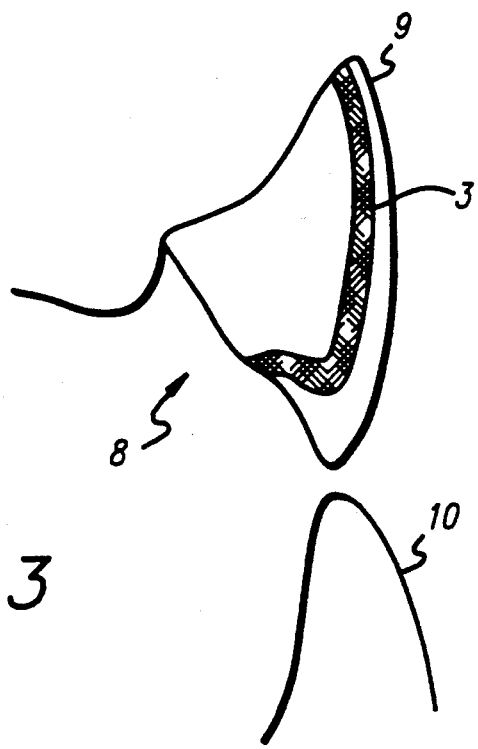
FIG. 3 is a diagrammatic sketch of an integral tip and facing in accordance with the present invention.

FIG. 3 shows a tooth 8 which has suffered a fractured tip and which has been repaired using a combined tip-facing according to the present invention. The natural tooth 8 is again ground to shape and a metal mesh 3 shaped over the tooth front surface and biting tip. A porcelain facing and integral tip is then formed on, or bonded to, the mesh which is then cemented to the damaged tooth 8. This repair results in a tooth of sufficient strength to allow normal mastication, in conjunction with the normally mating tooth 10.

I claim:

1. A method of manufacturing a dental prothesis comprising the steps of:
   shaping a textured corrosion resistant flexible insert to a general cup shape so as to fit over an outer surface of a prepared tooth remnant;
   forming a dental outer body shell of heat hardenable material which is partially fired, with an internal cavity and an external surface being of a tooth shape;
   coating the insert with a porcelain paint and positioning the insert into the cavity; and
   bonding the shell to the insert by further firing to complete the firing process of the body shell and bond the body shell to the insert.

2. A method as claimed in claim 1 wherein the insert is a mesh comprised of a woven tensile filament material.

3. A method as claimed in claim wherein the filament is corrosion resistant metal.

4. A method as claimed in any one of the preceding claims wherein the insert is firstly shaped about a tooth remnant of a patient and removed therefrom before positioning it into the cavity of the tooth shell for subsequent firing.

5. A method as claimed in claim 3 wherein the insert is firstly shaped about a casting of a tooth remnant of a patient and removed therefrom before positioning into the cavity of the shell body for subsequent firing.

6. A method of claim 1 wherein the heat hardenable material is porcelain.

7. A method as defined in claim 6 wherein a plurality of said shell bodies are produced at one location in a range of body sizes to provide a stock supply of body shells, a plurality of said inserts, or material from which said inserts is produced, is provided with said stock supply, and a suitable insert is selected, or formed, and bonded to a suitable shell body, at another location, to suit the requirements of a particular patient.

8. A method as defined in claim wherein a plurality of said body shells are produced at one location in a range of body sizes to provide a stock supply of body shells, a plurality of said inserts is provided with said stock supply, and a suitable insert is selected, or forward, and bonded to a suitable body shell, at another location, to suit the requirements of a particular patient.

9. A method as claimed in claim 2 wherein the insert is firstly shaped about a casting of a tooth remnant of a patient and removed therefrom before positioning into the cavity of the shell body for subsequent firing.

* * * * *